US006679827B2

(12) United States Patent
Sandstrom

(10) Patent No.: US 6,679,827 B2
(45) Date of Patent: Jan. 20, 2004

(54) MAGNETIC FIELD ENHANCEMENT OF TUMOR TREATMENT

(76) Inventor: Robert E. Sandstrom, 49 View Ridge La., Longview, WA (US) 98632

( * ) Notice: Subject to any disclaimer, the term of this patent is extended or adjusted under 35 U.S.C. 154(b) by 0 days.

(21) Appl. No.: 10/268,300

(22) Filed: Oct. 9, 2002

(65) Prior Publication Data

US 2003/0073879 A1 Apr. 17, 2003

Related U.S. Application Data

(60) Provisional application No. 60/328,085, filed on Oct. 11, 2001, and provisional application No. 60/349,270, filed on Jan. 18, 2002.

(51) Int. Cl.$^7$ .............................. A61N 2/04; A61B 17/52
(52) U.S. Cl. .......................................................... 600/9
(58) Field of Search ...................... 600/9–15; 128/897, 128/898

(56) References Cited

U.S. PATENT DOCUMENTS

| | | | |
|---|---|---|---|
| 4,665,898 A | * | 5/1987 | Costa et al. ................... 600/14 |
| 5,072,739 A | | 12/1991 | John |
| 5,087,336 A | | 2/1992 | Liboff et al. |
| 5,099,756 A | | 3/1992 | Franconi et al. |
| 5,156,587 A | * | 10/1992 | Montone ..................... 600/13 |
| 5,236,410 A | | 8/1993 | Granov et al. |
| 5,312,534 A | | 5/1994 | Liboff et al. |
| 5,437,600 A | | 8/1995 | Liboff et al. |
| 5,681,845 A | | 10/1997 | Janzen et al. |
| 5,718,246 A | | 2/1998 | Vona |
| 5,919,679 A | | 7/1999 | Blackman et al. |
| 5,921,244 A | | 7/1999 | Chen et al. |
| 5,968,527 A | | 10/1999 | Litovitz |
| 6,007,476 A | | 12/1999 | Wascher et al. |
| 6,043,066 A | | 3/2000 | Mangano et al. |
| 6,083,149 A | | 7/2000 | Wascher et al. |
| 6,099,459 A | | 8/2000 | Jacobson |
| 6,238,899 B1 | | 5/2001 | Blackman et al. |
| 6,239,145 B1 | | 5/2001 | Utsumi et al. |
| 6,261,831 B1 | * | 7/2001 | Agee ........................ 435/285.2 |
| 6,315,978 B1 | | 11/2001 | Grissom et al. |
| 6,322,676 B1 | | 11/2001 | Leddy et al. |
| 6,353,763 B1 | | 3/2002 | George et al. |
| 6,355,166 B1 | | 3/2002 | Amarasinghe et al. |
| 6,391,895 B1 | | 5/2002 | Towart et al. |
| 6,403,553 B1 | * | 6/2002 | Opitz et al. ..................... 514/2 |
| 2001/0044643 A1 | | 11/2001 | Litovitz |

FOREIGN PATENT DOCUMENTS

FR WO 00/04951 2/2000

OTHER PUBLICATIONS

Scaiano, Cozens, and McLean, "Model for the rationalization of magnetic field effects in vivo. Application of the radical pair mechanism to biological systems", Photochemistry and Photobiology, vol. 59, No. 6, pp 585–589, 1994.

Schulten, "Magnetic Field Effects in Chemistry and Biology", Festkorperprobleme (Advances in Solid State Physics), vol. XXII, Vieweg, Braunschweig, 1982.

Stass, Woodward, Timmel, Hore, McLauchlan, "Radiofrequency magnetic field effects on chemical reaction yields", Chemical Physics Letters 329 (2000) pp 15–22.

Steller, "Mechanisms and Genes of Cellular Suicide", Science, vol. 267(5203), Mar. 10, 1995, pp 1445–1449.

(List continued on next page.)

*Primary Examiner*—Samuel G. Gilbert
(74) *Attorney, Agent, or Firm*—Law Office of Timothy E. Siegel; Timothy E. Siegel

(57) ABSTRACT

A method of creating an elevated concentration of free radicals having augmented lifetimes within a tumor, that includes creating an elevated concentration of free radicals in the tumor and creating a magnetic field that traverses the tumor and that inhibits the recombination of the free radicals in the tumor. A magnetic field of 0.1 mTesla to 10 mTesla is generally used for this purpose.

16 Claims, 1 Drawing Sheet

OTHER PUBLICATIONS

Till, Timmel, Brocklehurst, Hore, "The influence of very small magnetic fields on radical recombination reactions in the limit of slow recombination", Chemical Physics Letters 298 (1998) pp 7–14.

Timmel, Cintolesi, Brocklehurst, Hore, "Model calculations of magnetic field effects on the recombination reactions of radicals with anisotropic hyperfine interactions", Chemical Physics Letters 334 (2001) pp 387–395.

Turro, "Supramolecular organic photochemistry: Control of covalent bond formation through noncovalent supramolecular interactions and magnetic effects", PNAS, Apr. 16, 2002, vol. 99, pp 4805–4809.

Abstract for Gewirtz, "A critical evaluation of the mechanisms of action proposed for the antitumor effects of the anthracycline antibiotics adriamycin and daunorubicin.", Biochem Parmacol, Apr. 1, 1999; 57 (7), pp727–41.

Abstract for Mates and Sanchez–Jimenez, "Role of reactive oxygen species in apoptosis:implications for cancer therapy.", Int J Biochem Cell Biol, Feb. 2000, 32 (2), pp 157–70.

Abstract for Chatgilialoglu and O'Neill,"Free radicals associated with DNA damage.",Exp Gerontol, Sep. 2001, 36(9), pp 1459–71.

abstract for Polk, "Dosimetry of extremely–low–frequency magnetic fields.",Bioelectromagnetics, 1992, Suppl 1, pp 209–235.

Grunberg, "Layered Magnetic Structures: History, Highlights, Applications", Physics Today Online,vol. 54, iss–5, p 31, Mar., 2002.

Halliwell, "Free Radicals and other reactive species in Disease", Encyclopedia of Life Sciences, 2001.

Harkins and Grissom, "Magnetic Field Effects on B12 Ethanolamine ammonia lyase: Evidence for a Radical Mechanism", Science, vol. 263 (5149), Feb. 18, 1994, pp 958–960.

LaVerne and Brocklehurst, "Magnetic Field Effects on the Solute Luminescence of Alkane Solutions Irradiated with Heavy Ions", J. Phys. Chem. 1996, 100, pp 1682–1688.

McCord, "The Evolution of Free Radicals and Oxidative Stress", The American Journal of Medicine, vol. 108(8), Jun. 1, 2000, pp 652–659.

Barry and O'Neill, "A Sting in the Tail of Electron Tracks", Science, vol. 287 (5458), Mar. 3, 2000, pp 1603–1604.

Mohtat, "Study of Magnetic Field Effects on Radical Reactions and of the Mobility of Transients in Microheterogeneous Systems", thesis, University of Ottawa, 1998.

Raylman and Wahl, "Magnetically enhanced radionuclide therapy", J Nucl Med, Jan. 1994, 35(1), pp 157–163.

Raylman, Clavo, Crawford, Recker, Wahl, "Magnetically-enhanced radionuclide therapy (MERiT): in vitro evaluation.", In J Radiat Oncol Biol Phys, Mar. 15, 1997, 37(5), pp 1201–1206.

Reed, "Mechanisms of apoptosis avoidance i n cancer", Curr Opin Oncol, vol. 11(1), Jan. 1999, 68.

Scaiano, Mohtat, Cozens, McLean, and Thansandote, "Application of the Radical Pair Mechanism to Free Radicals in Organized Systems: Can the Effects of 60 Hz Be Predicted From Studies Under Static Fields?", Bioelectromagnetics 15:549–554 (1994).

Scaiano, Cozens, and Mohtat, "Influence of combined AC–DC magnetic fields on free radicals in organized and biological systems. Development of a model and application of the radical pair mechanism to radicals in micelles.", Photochemistry and Photobiology, vol. 62, No. 5, pp 818–829, 1995.

Brocklehurst, "Magnetic fields and radical reactions: recent developments and their role in nature", Chem. Soc. Rev., 2002 31(5), pp301–311.

Buchachenko, "Magnetic Isotope Effect: Nuclear Spin Control of Chemical Reactions", The Journal of Physical Chemistry, vol. 105, No. 44, Nov. 8, 2001.

Burnshtein, Krissinel, and Steiner, "Diffusion, spin and reaction control in geminate reverse electron transfer", Phys. Chem. Chem. Phys., 2001, 3, pp198–203.

Canfield, Belford, Debrunner, Schulten, "A perturbation theory treatment of oscillating magnetic fields in the radical pair mechanism", Chemical Physics 182 (1994) pp 1–18.

Canfield, "Approaching magnetic field effects in biology using the radical pair mechanism", Thesis, University of Illinois at Urbana–Champaign, 1997.

Cozens and Scaiano, "A Comparative Study of Magnetic Field Effects on the Dynamics of Geminate and Random Radical Pair Processesin Micelles", J. Am. Chem. Soc. 1993, 115, pp 5204–5211.

Elsendoorn, Weijl, Mithoe, Zwinderman, Van Dam, De Zwart, Tates, Osanto,"Chemotherapy–induced chromosomal damag in peripheral blood lymphocytes of cancer patients supplemented with atioxidants or placebo", Mutation Research 498 (2001) pp 145–158.

Eveson, Timmel, Brocklehurst, Hore and McLauchlan, "The effects of weak magnetic fields on radical recombination reactions in micelles", Int. J. Radiat. Biol. 2000, vol. 76, No. 11, pp 1509–1522.

Eveson and McLauchlan, "Electron spin polarization studies of the dynamics of geminate free radical reactions", RIKEN Review No. 24 (Sep., 1999).

Gewirtz, "A Critical Evaluation of the Mechanisms of Action Proposed for the Antitumor Effects of the Anthracycline Antibiotics Adriamycin and Daunorubicin", Biochemical Pharmacology, vol. 57, pp 727–741, 1999.

Grissom, "Magnetic Field Effects in Biology: A Survey of Possible Mechanisms with Emphasis on Radical–Pair Recombination", Chem. Rev. 1995, 95, pp 3–24.

Brocklehurst and McLaughlan, "Free radical mechanism for the effects of environmental electromagnetic fields on biological systems," Int. J. Radiat. Biol Dec. 1996, vol. 69, No. 1, pp3–24.

* cited by examiner

MAGNETIC FIELD ENHANCEMENT OF TUMOR TREATMENT

RELATED APPLICATIONS

This application claims the benefit of provisional application 60/328,085 filed Oct. 11, 2001 and of provisional application 60/349,270 filed Jan. 18, 2002.

BACKGROUND OF THE INVENTION

A central problem in cancer treatment is that of preserving healthy tissue while destroying cancerous tissue. Although radiation therapy generally involves the focusing of radiation on a tumor, at least some healthy tissue generally is located in the irradiated field. This healthy tissue is exposed to and to some degree damaged by the radiation. In chemotherapy healthy tissue is exposed to the chemotherapy agent and may be damaged.

Moreover, research has shown that much of the effect of radiation therapy and a substantial component of some approaches to chemotherapy are mediated by free radical effects in tumor tissue. The mechanisms whereby free radicals produce tumor cell death include direct enzymatic effects, DNA damage and induction of apoptotic pathways.

Our understanding of the physics and chemistry of free radicals and paired radicals has gradually increased over the past ten years. A free radical is any chemical species capable of an independent existence that has an unpaired electron in its valence shell. The presence of an unpaired electron in the valence shell causes free radicals to be paramagnetic and exhibit magnetic properties when exposed to a magnetic field.

Free radicals may be formed by any of several mechanisms including but not limited to:

Ultraviolet induced homolytic fission as may be encountered in laser ablation therapy of tumors;

Specific chemical reactions as encountered with pharmacological chemotherapy e.g. bleomycin;

Ionizing radiation as the result of external beam irradiation, antibody directed or site selective radionucleotide administration or through implantation radiotherapy e.g. prostatic brachyotherapy;

Thermal induction as in hyperthermic therapy; or

Ultrasound induced acoustic cavitation.

Free radicals once generated may recombine. The biologic effects of free radicals in tissue are determined by the net reactive fraction namely the "escape" population that does not recombine rapidly. Factors, which influence pair recombination, include the viscosity of the reaction environment, temperature, bystander effects and the quantum state of the free radical. The quantum state of the free radical is defined by the applicable Schrodinger equation ($H\Psi=E\Psi$) where H is a Hamiltonian operator and $\Psi$ are sets of wave functions (Eigenfunctions). The Eigenfunctions are defined by a set of four quantum numbers: n-the principal quantum number, 1-the orbital quantum number, $M_1$-the magnetic quantum number and $M_s$-the spin quantum number. Of particular significance to this discussion is the spin quantum number.

The spin quantum number for an unpaired orbital electron can assume one of two values either $+\frac{1}{2}$ or $-\frac{1}{2}$. The wave distribution function determined by spin quantitization is a vector quantity and subject to influence by a superimposed magnetic field. When two electrons share an orbital space they must have opposite spin polarity. This phenomenon is dictated by the Pauli Exclusion Principal that postulates that no two electrons can occupy the same quantum state.

Spin polarity is conventionally referred to as up spin (↑) $+\frac{1}{2}$ or down spin (↓)$-\frac{1}{2}$. Shared valence electrons in the formation of chemical bonds also must have opposite spin polarity. When covalent bonds are severed as in the formation of free radicals spin polarity is preserved.

The unpaired electron in the valence orbital of a free radical in a magnetic field will precess in a manner comparable to Larmor precession described for charged particles in classic electrodynamics. Quantum precession leads to spin phase transitions between the singlet state where antiparallel spin vectors apply and triplet states where parallel spin vectors apply. The singlet state is favorable for recombination because antiparallel spin orientation is preserved and a covalent bond can be established. Triplet state configurations are unfavorable for recombination because parallel spin orientation is induced. In a magnetic field there are three triplet state configurations, which are vector quantities that due to precession in the magnetic field are no longer energy equivalent and are said to be nondegenerate.

The strength of the applied magnetic field, which maximizes the spin phase mixing effect, is dependent on the quantum state of the free radical or the system of free radicals. In general optimum phase mixing is achieved at relatively low magnetic field strengths (0.1–10.0 mTesla) within the hyperfine coupling energy levels of the radical pair.

The singlet state ($S_1$) characterized by antiparallel spin vectors will prevail in the absence of a magnetic field when homolytic fission of a covalent bond occurs to form a free radical pair. In the presence of a magnetic field of appropriate strength, the triplet states, $T_{-1}$, $T_0$ and $T_{-1}$ are equally probable energy states and are distinct and nondegenerate. The theoretic distribution between singlet and triplet states will be 25% singlet and 75% triplet. Such a distribution will theoretically increase the effective concentration of escape radicals by 75%. In experimental situations the yield is limited by non-quantum factors including viscosity effects, temperature, diffusion and bystander effects. However, increases in escape radical reactivity of 20–40% are documented in experimental systems where free radical escape reactions are measured.

SUMMARY

The present invention is a method of treating a tumor in which an elevated concentration of free radicals is created in the tumor by one of several methods described. In addition, a magnetic field is created that traverses the tumor and that inhibits the recombination of the free radicals in the tumor enhancing escape radical reactivity, which results in enhanced tumoricidal effect.

The foregoing and other objectives, features and advantages of the invention will be more readily understood upon consideration of the following detailed description of the invention, taken in conjunction with the accompanying drawings.

DETAILED DESCRIPTION OF THE PREFERRED EMBODIMENTS

Figure 1:
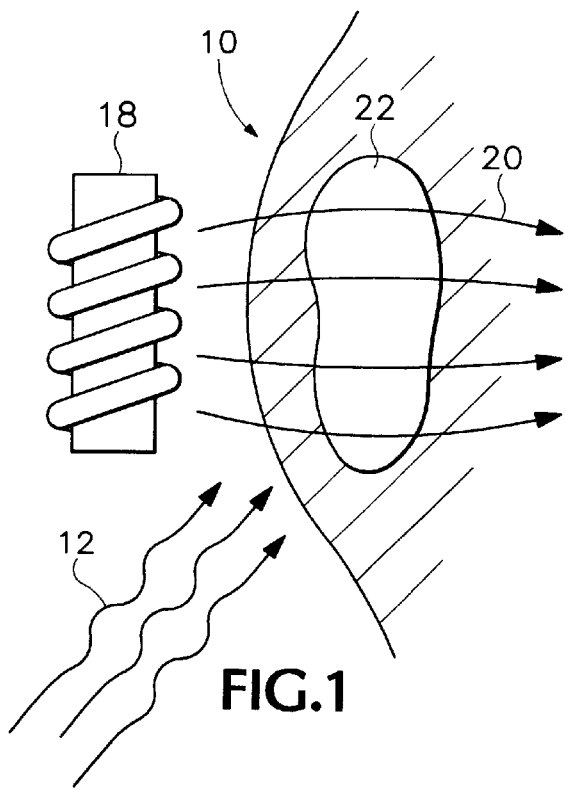
FIG. 1 is an illustration of a tumor being treated by radiation therapy augmented by a magnetic field.

Referring to FIG. 1, in a first preferred embodiment a patient's body 10 is subjected to radiation 12 that travels through the body 10 in a first direction. A magnet 18 is oriented so as to create a magnetic field 20 in the vicinity of a tumor 22 of one milli Tesla (mT). The magnet 18 is aligned so that the area of intersection of the radiation and the magnetic field conforms to the outline of the tumor. Typically in this operation-magnets 18 are electromagnets, as they may be controlled to vary the intensity of the magnetic field over time. In one preferred embodiment, however, static magnets are used as they can be more easily shaped to reflect the cross section of the tumor. The magnetic field may also be induced by magnetite, sprayed or painted magnetic films or implants or any other method of creating a magnetic field. In addition, magnetic shielding may be introduced to block ambient magnetic field effects.

The radiation 12 used may be gamma ray, x-ray or photon radiation. In addition, as used in this application, the term radiation also encompasses sound waves as in ultrasound-induced acoustic cavitation, and radiation 12 may take this form.

Figure 2:
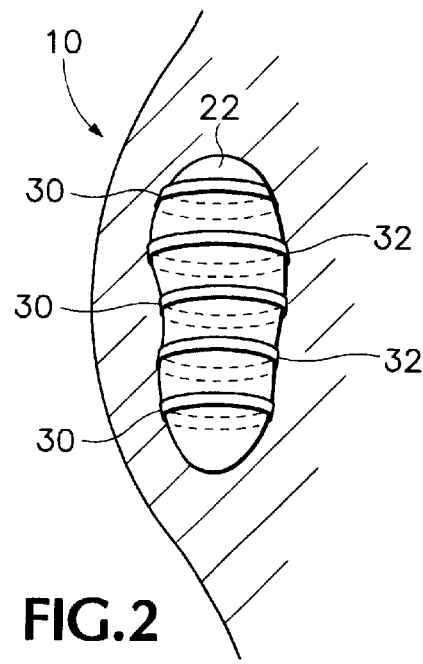
FIG. 2 is an illustration of a tumor being treated by strips of implanted radioactive material interspersed with strips of implanted magnetic material.

Referring to FIG. 2, a tumor 22 may be treated by placing radioactive strips 30 about it. Additionally, magnetic strips 32 are placed to create a magnetic field in the tumor 22.

Figure 3:
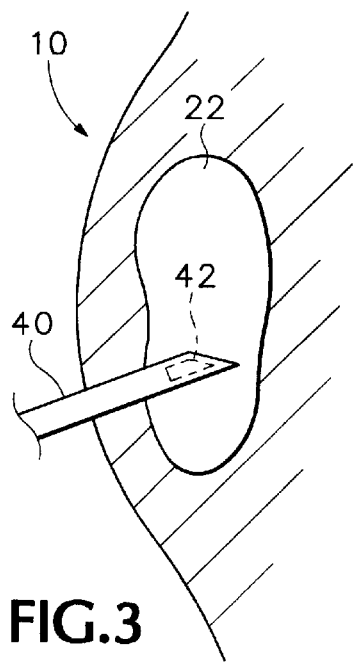
FIG. 3 is an illustration of a tumor into which a magnet has been introduced by a laparoscope.

Referring to FIG. 3, a laparoscope 40 is used to introduce a magnet 42 directly into the tumor. The tumor is then additionally treated with an injection of chemotherapy agents, which could also be from the laparoscope 40 or with radiation as in FIG. 1. Laparoscope 40 may also include a light source, for performing photon source radiation. In one preferred embodiment, laparoscope 40 injects a chemical agent that is activated by light waves to yield free radicals and also includes a light source for activating the chemical agent.

Figure 4:
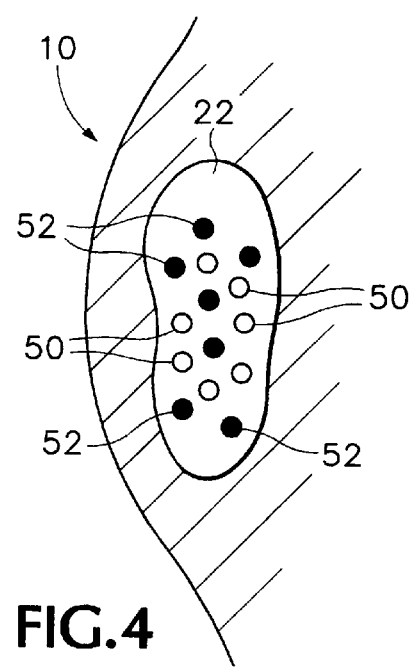
FIG. 4 is an illustration of a tumor that is being treated by a combination of radioactive beads and magnetic beads.

FIG. 4 shows a tumor that is being treated by a set of radioactive beads 50 and a set of magnetic beads 52, adapted to create a magnetic field.

For any of the above-described techniques, the magnetic field created is preferably between about 0.1 mTesla and 10 mTesla (10–1,000 gauss).

In an additional preferred embodiment, substances that form free radical pairs in the presence of radiation (including among other forms, light radiation) are injected into the tumor or into the vicinity of the tumor. In a variant of this embodiment, the substance that is injected forms free radical pairs that are particularly likely to cause apoptosis (cell death). In another variant, the substance that is injected forms free radical pairs that are particularly sensitive to a magnetic field. The free radical pairs produced may be easily induced into the triplet state by way of the application of a low intensity magnetic field.

In tumor treatment systems where the effectors of tumor cell killing are the escape free radicals, analysis indicates that a magnetic field on the order of 0.1 to 1.0 milliTesla will cause a 30–40% increase in tumor lethality. Accordingly, in one preferred variant of a treatment system using radiation mediated free radical production, the equivalent tumoricidal effect is achieved at significantly lower overall radiation levels. In another variant, higher tumoricidal effect is achieved at equivalent radiation levels.

Furthermore, since the magnetic effect is a vector quantity, the magnetic field, in one preferred embodiment, is contoured to fit the topography of an irradiated tumor allowing more focused radiation effect and sparing normal tissues. This topologic modeling complements and improves prior art radiation treatment field design by introducing an independent vector specific variable.

As noted, at least one preferred embodiment makes use of oscillating or alternating magnetic fields to influence radical reactivity. However, the frequency of the oscillating or alternating field will be dependent on the short radical recombination time window. Subtle combinatorial magnetic effects, which combine static and modulated magnetic field effects, may offer advantages in specific situations.

At least one preferred embodiment makes use of modifications of the ambient magnetic field environment to optimize the magnetic effect described. In cases where electronic equipment near to the intended tumor target modifies the electromagnetic environment, shielding is used to prevent ambient electromagnetic interference. In one preferred embodiment, low carbon steel shields are used for this purpose. In another preferred embodiment mumetal shielding is employed.

Radical pair recombination as mentioned will be influenced by the biologic reaction environment and modifications to viscosity, temperature and structural properties including cell membranes and organelles may be exploitable parameters to further enhance the tumoricidal benefit described here.

In a further preferred embodiment, the magnetic field and the substances injected are specifically adapted to destroy specific cell constituents that are targeted by known targeting mechanisms, e.g. antigen-antibody targeting.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method of creating an elevated concentration of free radicals having augmented lifetimes within a tumor, comprising:

(a) creating an elevated concentration of free radicals in said tumor; and (b) creating a magnetic field that traverses said tumor and that inhibits the recombination of said free radicals in said tumor, thereby augmenting said lifetimes of said free radicals.

2. The method of claim 1, wherein said free radicals are created in said tumor by means of electromagnetic radiation.

3. The method of claim 2, wherein said electromagnetic radiation is in a frequency band from $10^{10}$ Hz to $10^{20}$ Hz.

4. The method of claim 2, wherein said electromagnetic radiation is in a frequency band from $2*10^{14}$ to $10^{15}$ Hz.

5. The method of claim 2, wherein said electromagnetic radiation is applied to said tumor in conjunction with the introduction of a chemical agent.

6. The method of claim 1, wherein said free radicals are created in said tumor by means of the introduction of a chemical agent.

7. The method of claim 1, wherein said magnetic field is of a magnitude that facilitates the interstate crossing of singlet state free radical pairs to triplet state free radical pairs.

8. The method of claim 1, wherein said magnetic field has a magnitude in the range of 0.1 Tesla to 10 milli Tesla through said tumor.

9. The method of claim 1, wherein said magnetic field is of a magnitude that inhibits the interstate crossing of triplet state free radical pairs to singlet state free radical pairs.

10. The method of claim 1, wherein said magnetic field is created by at least one magnet positioned exterior to said tumor.

11. The method of claim 1, wherein said magnetic field is created by magnetic particles that are injected into proximity to said tumor.

12. The method of claim 1, wherein said elevated concentration of free radical pairs is created by sound waves.

13. The method of claim 1, wherein said elevated concentration of free radical pairs is created by acoustic cavitation.

14. The method of claim 1, wherein said free radicals interfere with the operation of enzymes within said tumor cells.

15. The method of claim 1, wherein said magnetic field is contoured, scaled or designed to conform to tumor volume or shape.

16. The method of claim 1, wherein electromagnetic shielding is used about said tumor to block ambient electromagnetic interference from said tumor.

* * * * *

UNITED STATES PATENT AND TRADEMARK OFFICE
CERTIFICATE OF CORRECTION

PATENT NO. : 6,679,827 B2
DATED : January 20, 2004
INVENTOR(S) : Sandstrom

It is certified that error appears in the above-identified patent and that said Letters Patent is hereby corrected as shown below:

<u>Column 2,</u>
Line 31, change the last triplet state to -- $T_{+1}$. -- . should read -- strength, the triplet states, $T_{-1}$, $T_0$, and $T_{+1}$ are equally --

<u>Column 3,</u>
Line 11, remove the hyphen. The line should read -- in this operation magnets 18 are electromagnets, as --

Signed and Sealed this

Eighteenth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO.        : 6,679,827 B2
APPLICATION NO.   : 10/268300
DATED             : January 20, 2004
INVENTOR(S)       : Sandstrom It is certified that error appears in the above-identified patent and that said Letters Patent is hereby corrected as shown below:

On The Title Page; Item (56)
Page 1        Add References Cited:

| | | | |
|---|---|---|---|
| 6,200,547 B1 | 3/2001 | Volkonsky et al. | 424/9.36 |
| 6,482,436 B1 | 11/2002 | Volkonsky et al. | 424/489 |
| 6,488,615 B1 | 12/2002 | Mitchiner et al. | 600/9 |

Signed and Sealed this

Fifth Day of June, 2007

JON W. DUDAS
*Director of the United States Patent and Trademark Office*